United States Patent [19]

Washizuka et al.

[11] Patent Number: 4,813,400
[45] Date of Patent: Mar. 21, 1989

[54] OPTICAL FIBER ASSEMBLY FOR AN ENDOSCOPE

[75] Inventors: Nobuhiko Washizuka; Koji Kambara, both of Tokyo, Japan

[73] Assignee: Olympus Optical Co., Ltd., Japan

[21] Appl. No.: 79,139

[22] Filed: Jul. 29, 1987

[30] Foreign Application Priority Data

Aug. 8, 1986 [JP] Japan .................. 61-186508
Aug. 8, 1986 [JP] Japan .............. 61-121673[U]

[51] Int. Cl.$^4$ .................................................. A61B 1/06
[52] U.S. Cl. ................................... 128/6; 350/96.26
[58] Field of Search ......................... 128/6; 350/96.26

[56] References Cited

U.S. PATENT DOCUMENTS

| | | | |
|---|---|---|---|
| 2,975,785 | 3/1961 | Sheldon et al. | 128/6 |
| 3,004,368 | 10/1961 | Hicks, Jr. | |
| 3,068,739 | 12/1962 | Hicks | 128/6 UX |
| 3,434,775 | 3/1969 | Gosselin | 128/6 |
| 3,624,816 | 11/1971 | Strack | |
| 4,732,139 | 3/1988 | Kawashima et al. | 128/6 |
| 4,756,303 | 7/1988 | Kawashima et al. | 128/6 |

FOREIGN PATENT DOCUMENTS

| | | |
|---|---|---|
| 1956963 | 11/1971 | Fed. Rep. of Germany . |
| 7919694 | 7/1979 | Fed. Rep. of Germany . |
| 57-100711 | 6/1982 | Japan . |
| 58-1905 | 1/1983 | Japan . |
| 60-233603 | 1/1985 | Japan . |

*Primary Examiner*—William H. Grieb

[57] ABSTRACT

An endoscope, through which the interior of a body cavity can be observed, has an operation section and an insertion section. The proximal end of the insertion section is connected to the distal end of the operation section. A conduit-type guide fiber is coupled at one end to the distal end of the insertion section. The other end of the guide fiber is connected to the operation section. The guide fiber has meandering or looped portion for absorbing the stress applied to the fiber when the insertion section is bent. Therefore, there is no possibility that the guide fiber is broken. In addition, the insertion section has a sufficient flexibility.

7 Claims, 4 Drawing Sheets

OPTICAL FIBER ASSEMBLY FOR AN ENDOSCOPE

BACKGROUND OF THE INVENTION

The present invention relates to an endoscope having an operation section and an insertion section, and more particularly to an endoscope having a flexible fiber optic conduit coupled at one end to the proximal end of an operation section and at the other end to the distal end of an insertion section.

2. Description of the Prior Art

A typical endoscope comprises an insertion section and an operation section. It further comprises a guide fiber having, for example, an image guide fiber or a light guide fiber, and extending from the operation section to the distal end of the insertion section. One end of the guide fiber is fastened to the proximal end of the operation section, and the other end thereof is secured to the distal end of the insertion section. The guide fiber is made of a number of quartz glass element fibers. The element fibers are bonded together by filling the gaps among them with molten cladding agent. Were the element fibers not bonded, the periphery of each fiber should be coated with a lubricant layer, thereby to prevent the wear of the individual element fibers. Were element fibers coated with lubricant layers, the guide fiber as a whole should have a large outer diameter. Therefore, the molten cladding agent is filled in the gaps among the element fibers, thereby forming a so-called "conduit-type" guide fiber having a small outer diameter. Since the guide fiber of this type is used in the endoscope, the insertion section thereof can have a small diameter.

However, the guide fiber of the conduit type is rigid. When it is used in an endoscope, with its both ends fixed, the insertion section of the endoscope inevitably becomes less flexible. Further, the conduit-type guide fiber may be broken when the insertion section is bent excessively.

Japanese Patent Disclosure (Kokai) No. 58-1905 discloses an endoscope designed to solve these problems with a conduit-type guide fiber. In this endoscope, one end of the conduit-type guide fiber, or a rigid, image guide fiber, is fastened to a holder holding an objective lens, and the other end of the fiber is slidably supported by a holder holding an ocular lens. Since the other end of the fiber can slide with respect to the ocular holder, no bending stress is exerted on the fiber when the insertion section is bent. When the other end of the fiber slides, however, the distance between this end of the fiber and the ocular lens changes. Consequently, the image of the interior of the body cavity, which is being examined through the endoscope, comes out of focus. Moreover, when the image guide fiber is combined with a light guide fiber, the amount of light input to the light guide fiber inevitably changes as the end of the image guide fiber slides with respect to the ocular holder.

SUMMARY OF THE INVENTION

It is accordingly the object of the present invention to provide an endoscope having a conduit-type guide fiber which is fastened at one end to an operation section and at the other end to an insertion section, and which is flexible enough to render the insertion section sufficiently flexible and not to be broken when the insertion section is bent.

The above object can be attained by an endoscope which comprises an insertion section having a distal end and a proximal end, and an operation section coupled to the proximal end of the insertion section. The endoscope further comprises a conduit-type guide fiber. One end of the guide fiber is coupled to the distal end of the insertion section, and the other end thereof is coupled to the operation section. The guide fiber has meandering or looped portion for absorbing the stress generated when the insertion section is bent.

In the endoscope according to the invention, the bending stress, which is applied to the guide fiber when the insertion section is bent, is absorbed. Therefore, there is no possibility that the guide fiber is broken, though the ends of the guide fiber are fastened to the insertion section and the operation section, respectively. For the same reason, the insertion section can have a sufficient flexibility.

DETAILED DESCRIPTION OF THE PREFERRED EMBODIMENTS

Embodiments of the present invention will now be described with reference to the drawings attached hereto.

Figure 1:
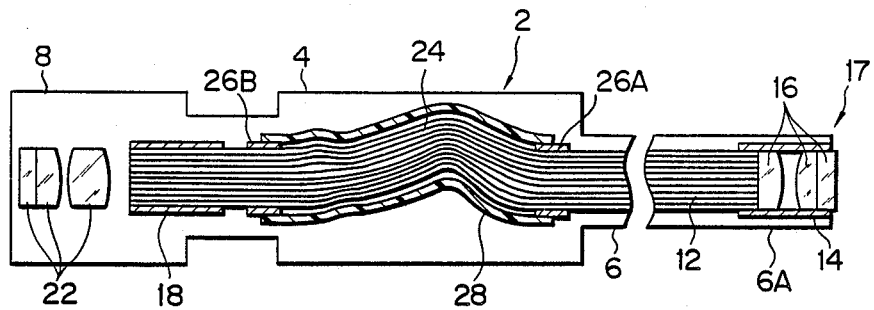
FIG. 1 is a longitudinal, sectional view schematically showing an endoscope according to a first embodiment of the present invention.
Figure 2:
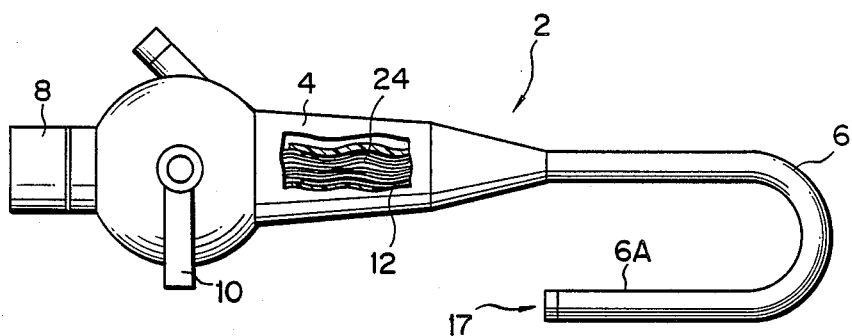
FIG. 2 is a side view of the endoscope shown in FIG. 1.
Figure 3:
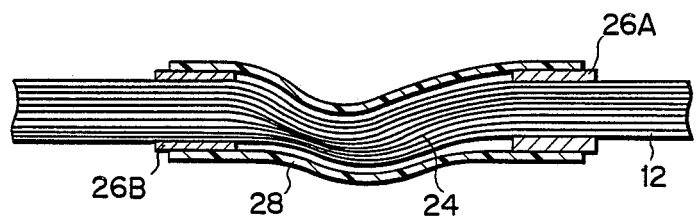
FIG. 3 is a longitudinal, sectional view showing the meandering portion of the guide fiber used in the endoscope shown in FIG. 1.

FIGS. 1 to 3 show an endoscope according to the first embodiment of the invention. As is illustrated in FIG. 2, this endoscope 2 comprises operation section 4, and insertion section 6 coupled to the distal end of operation section 4. Eyepiece section 8 and lever 10 are provided at the proximal end portion of operation section 4. Lever 10 is designed to bend the bendable portion 6A, or the distal end portion of insertion section 6.

Image guide fiber 12, or a flexible fiber optic conduit, is provided within endoscope 2. Fiber 12 extends from operation section 4 and through insertion section 6. The distal end of image guide fiber 12 abuts on lens system 17 provided within the distal end portion of insertion section 6. Lens system 17 comprises a plurality of objective lenses 16. Both the distal end portion of fiber 12 and lens system 17 are held within first holder 14. Second holder 18 is provided within eyepiece section 8 of operation section 4. The proximal end portion of image guide fiber 12 is held within second holder 18, such that the proximal end of fiber 12 opposes a plurality of ocular lenses 22 also provided within eyepiece section 8. First holder 14 is fixed within the distal end portion of insertion section 6, and second holder 18 is fixed within the proximal end portion of operation section 4.

Image guide fiber 12 has, at its middle portion, a means for absorbing the stress exerted on fiber 12 in the longitudinal or transverse direction thereof. More specifically, the middle portion 24 of fiber 12 is meandering. In this meandering portion 24, no cladding agent is applied to bond the element fibers of image guide fiber 12. Hence, the element fibers forming meandering portion 24 can slide on one another, and meandering portion 24 is therefore more flexible than the other portions of image guide fiber 12. The element fibers are fastened together by metal bands 26A and 26B at the ends of meandering portion 24. Meandering portion 24 is covered and protected by protective tube 28. Protective tube 28 is made of elastic material such as rubber or a synthetic resin, and is fixed at both ends to metal bands 26A and 26B.

The operation of endoscope 2 will now be explained. When lever 10 is operated, thereby bending insertion section 6, stress is applied to image guide fiber 12 extending through insertion section 6. At this time, meandering portion 24 of fiber 12, which is provided within operation section 4, is straightened, thus absorbing the stress. In other words, the stress applied to image guide fiber 12 can be absorbed by meandering portion 24 though fiber 12 is of the conduit type and is relatively rigid. This is because meandering portion 24, which is provided within operation section 4, can be deformed as insertion section 6 is bent. Therefore, no excessive stress is applied to image guide fiber 12 thereby to break fiber 12. In addition, insertion section 6 can have a sufficient flexibility for the same reason.

FIGS. 4 to 8 show various modifications of the guide fiber, which can be used in the first embodiment of the invention.

Figure 4:
FIGS. 4 to 8 are longitudinal, sectional views of various modifications of the guide fiber, which can be used in the endoscope of FIG. 1.

In the first modification of the guide fiber, shown in FIG. 4, bands 30 tying the element fibers at the ends of meandering portion 24 are made of elastic material such as rubber or a synthetic resin. Since bands 30 are elastic, there is no possibility that image guide fiber 12 is broken at the boundaries between soft meandering portion 24 and the other portions of fiber 12 which are relatively rigid.

Figure 5:
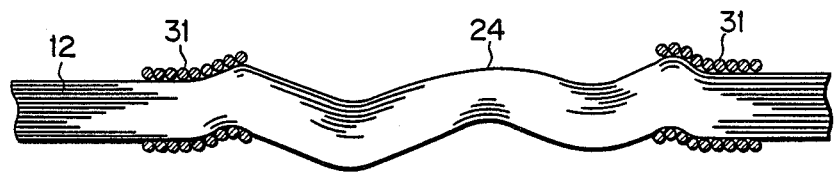

In the second modification of the guide fiber, shown in FIG. 5, coils 31 tie the element fibers at the ends of meandering portion 24. Coils 31 are made of a wire having a circular cross section.

Figure 6:
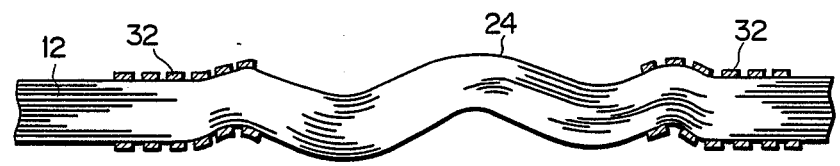

In the third modification of the guide fiber, illustrated in FIG. 6, coils 32 tie the element fibers at the ends of meandering portion 24. Coils 32 are made of a wire having a rectangular cross section.

Figure 7:
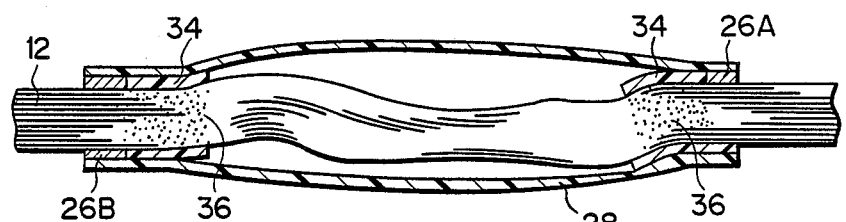

In the fourth modification of the guide fiber, shown in FIG. 7, bands 26A, 26B bundle the element fibers together at the ends of meandering portion 24. Short tubes 34 are mounted on those end parts of meandering portion 24 which are connected to the ends of portion 24. Short tubes 34 are rigid and formed so as to allow meandering portion 24 to bend in a specified direction. Adhesive 36 made mainly of epoxy resin or silicone fills the gaps among the element fibers forming those end parts of meandering portion 24 which are guided by short tubes 34. Further, meandering portion 24 is surrounded by protective tube 28. Therefore, both end parts and middle part of meandering portion 24 can be sufficiently protected. Adhesive 36 can be of the type that hardens when irradiated with ultraviolet rays.

Figure 8:
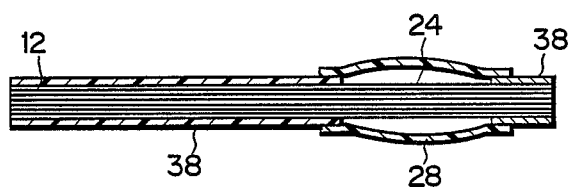
Figure 9:
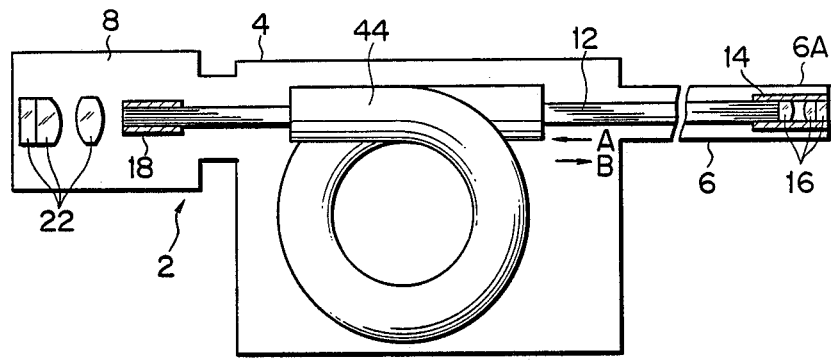
FIG. 9 is a longitudinal, sectional view schematically illustrating an endoscope according to a second embodiment of the invention.

In the fifth modification of guide fiber 12, illustrated in FIG. 8, meandering portion 24 is surrounded by protective tube 28, and the other portions of image guide fiber 12 is surrounded by heat-shrinkable tubes 38.

In the modifications of the guide fiber, shown in FIGS. 4, 5 and 6, meandering portion 24 can be sheathed within protective tube 28. Further, the present invention can apply not only an image guide fiber, but also to a light guide fiber.

The endoscope according to a second embodiment of the invention will now be described with reference to FIGS. 9 to 12.

Figure 10:
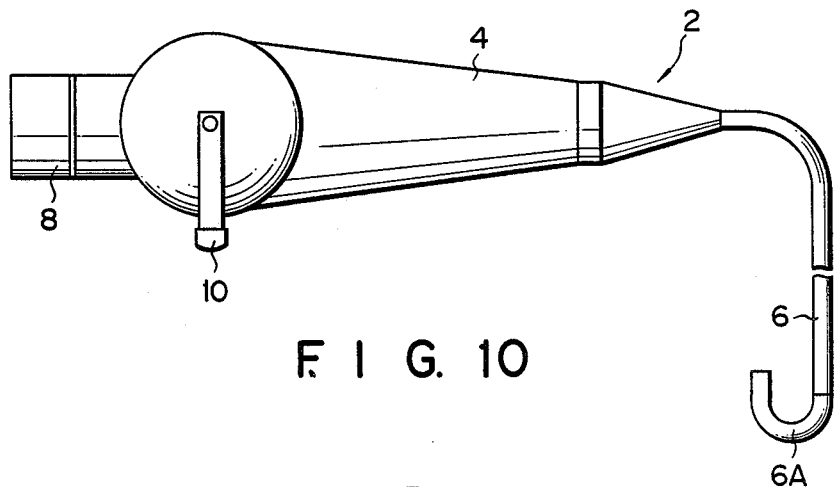
FIG. 10 is a side view of the endoscope shown in FIG. 9.

As is shown in FIG. 10, the endoscope 2 of the second embodiment comprises operation section 4 and insertion section 6. Insertion section 6 is connected to the distal end of operation section 4. Eyepiece section 8 and lever 10 are provided at the proximal end portion of operation section 4. When lever 10 is pulled, the bendable portion 6A of insertion section 6 is bent.

Figure 11:
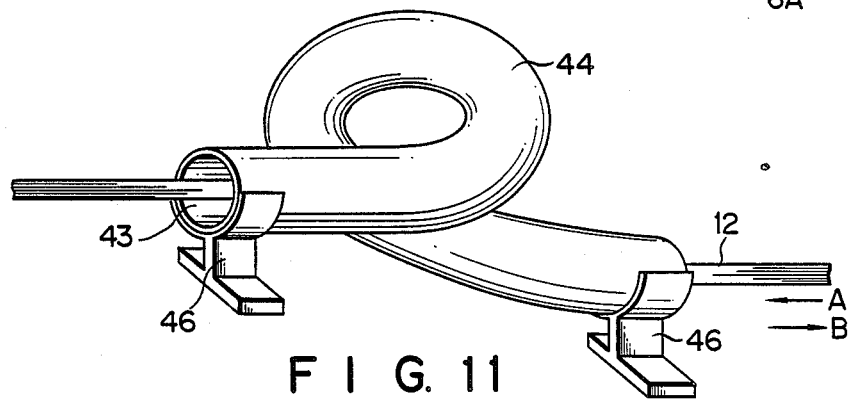
FIG. 11 is a perspective view showing the guide fiber and the guide member, both used in the endoscope of FIG. 9.

Within endoscope 2, conduit-type image guide fiber 12 is provided partly in operation section 4 and partly in insertion section 6. The distal end of image guide 12 is held by first holder 14, which is provided within the distal end portion of fiber 12 and also holds a plurality of objective lenses 16. The proximal end of image guide fiber 12 is held by second holder 18 provided within eyepiece section 8 of operation section 4. The proximal end of fiber 12 opposes a plurality of ocular lenses 22. The middle portion 42 of image guide fiber 12, which is located within operation section 4, is looped. Looped portion 42 is sheathed within tubular guide 44 having passage 43. Passage 43 has a diameter larger than that of fiber 12. As is shown in FIG. 11, both ends of tubular guide 44 are fastened to operation section 4 by fastening members 46. As long as insertion section 6 remains straight, image guide fiber 12 extends substantially along the axis of tubular guide 44.

The operation of endoscope according to the second embodiment will now be explained.

Figure 12:
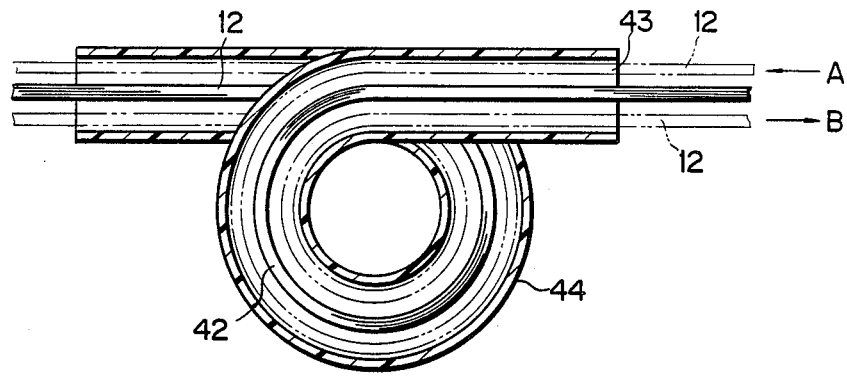
FIG. 12 is a longitudinal, sectional view of the guide fiber and the guide member, both shown in FIG. 11.

When lever 10 is either pushed or pulled, thereby bending insertion section 6 in one direction, image guide fiber 12 is moved in the direction of arrow A or arrow B as is shown in FIG. 12. Looped portion 42 provided within operation section 4, therefore, expands or contracts as is indicated by two-dot chain lines in FIG. 12, thereby absorbing the slacking of fiber 12, or, thus absorbing the stress applied to fiber 12. Looped portion 42 can easily be deformed as insertion section 6 is bent in one direction or another, and can therefore absorb the slacking of fiber 12 of the rigid, conduit type, and also the stress applied to this fiber 12.

Due to looped portion 42 of image guide fiber 12, no excessive stress is exerted on image guide fiber 12 to break fiber 12. In addition, insertion section 6 can have a sufficient flexibility.

Figure 13:
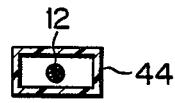
FIGS. 13 and 14 are cross-sectional views of two modifications of the guide member shown in FIGS. 11 and 12.
Figure 14:
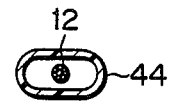
Figure 15:
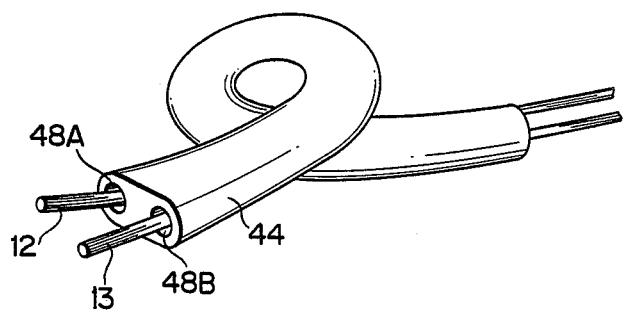
FIG. 15 is a perspective view showing a modification of the guide fiber shown in FIGS. 13 and 14, and another modification of the guide member used in the endoscope of FIG. 9.

FIGS. 13 to 15 show modifications of tubular guide 44 used in the second embodiment. The modification shown in FIG. 13 has a rectangular cross section. The modification shown in FIG. 14 has an elliptical cross section. The modification shown in FIG. 15 has two parallel passages 48A and 48B. Image guide fiber 12 and light guide fiber 13 extend through these passages 48A and 48B, respectively.

Only the image guide fiber has been mainly described in explaining the embodiment of the invention. Nonetheless, the present invention can apply to the protection of a light guide fiber.

What is claimed is:

1. An endoscope comprising:
    an operation section having a distal end and a proximal end;
    an insertion section having a distal end and a proximal end, said insertion section being connected at the proximal end to the distal end of said operation section;
    a conduit-type guide fiber having a first end provided within the distal end of said insertion section, a second end provided in said operation section, and a looped middle portion; and
    a looped tubular guide member including a passage having a diameter sufficiently larger than the diameter of said guide fiber, in which the looped middle portion of said guide fiber is inserted.

2. The endoscope according to claim 1, wherein a gap is provided between said looped tubular guide member and said looped middle portion of said guide fiber, whereby a stress applied to said guide fiber in the longitudinal or transverse direction can be absorbed, with the diameter of the looped middle portion being increased or decreased.

3. The endoscope according to claim 2, wherein both end portions of said looped tubular guide member are fixed on said operation section by fastening members.

4. The endoscope according to claim 2, wherein said looped tubular guide member has a passage having a substantially rectangular cross-section.

5. The endoscope according to claim 2, wherein said looped tubular guide member has a passage having a substantially oval cross-section.

6. The endoscope according to claim 2, wherein said guide fiber comprises an image guide fiber and a light guide fiber, and said guide member has two passages in which the image guide fiber and the light guide fiber are inserted, respectively.

7. An endoscope comprising:
    an operation section having a distal end and a proximal end;
    an insertion section having a distal end and a proximal end, said insertion section being connected at the proximal end to the distal end of said operation section;
    a conduit-type guide fiber having a first end provided within the distal end of said insertion section, a second end provided in said operation section, and a looped middle portion; and
    a looped tubular guide member including a passage in which the looped middle portion of said guide fiber is inserted, a gap being provided between said looped tubular guide member and said looped middle portion of said guide fiber, whereby a stress applied to said guide fiber in the longitudinal or transverse direction can be absorbed, with the diameter of the looped middle portion being increased or decreased.

* * * * *